United States Patent
Ishii et al.

[11] Patent Number: 6,100,419
[45] Date of Patent: Aug. 8, 2000

[54] PROCESSES FOR PRODUCING α-AMINONITRILE DERIVATIVES AND α-AMINO ACIDS

[75] Inventors: Yasutaka Ishii, Takatsuki; Tatsuya Nakano, Himeji, both of Japan

[73] Assignee: Daicel Chemical Industries, Ltd., Osaka, Japan

[21] Appl. No.: 09/213,904

[22] Filed: Dec. 17, 1998

[30] Foreign Application Priority Data

Dec. 26, 1997 [JP] Japan ................. 9-359860

[51] Int. Cl.⁷ ................. C07C 253/10; C07C 249/08
[52] U.S. Cl. ................. 558/332; 558/446
[58] Field of Search ................. 558/332, 446

[56] References Cited

PUBLICATIONS

Akito Fujii et al. *Chemical Abstracts*, vol. 129, No. 14, p. 677 (Dec. 14, 1998).
Gertwalt Zinner et al. *Chemiker Zeitung*, vol. 100, pp. 546–547, (Dec. 1976).
L. Neelakantan et al. *Journal of Organic Chemistry*, vol. 23, pp. 964–967, (Feb. 7, 1958).
P. G. Sammes. *Journal of the Chemical Society*, pp. 6608–6613, (1965).
B. Krzyzanowska et al. *Synthesis*, pp. 521–524, (1978).

*Primary Examiner*—Joseph McKane
*Assistant Examiner*—Joseph Murray
*Attorney, Agent, or Firm*—Birch, Stewart, Kolasch & Birch, LLP

[57] ABSTRACT

In the presence of a metal catalyst such as a samarium compound, an oxime ester compound shown by the formula (1):

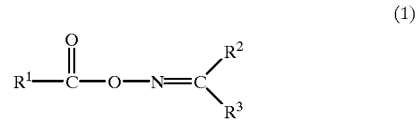

(1)

wherein $R^1$, $R^2$, and $R^3$ are the same or different from each other, and each represents a non-reactive atom or a non-reactive organic group; and $R^2$ and $R^3$, together with the adjacent carbon atom, may bond together to form a ring is reacted with a cyanogenation agent such as an α-cyanohydrin compound (e.g., acetone cyanohydrin) to form an α-aminonitrile derivative. By hydrolyzing the α-aminonitrile derivative, the corresponding α-amino acid or a salt thereof can be obtained. According to the above processes, an α-aminonitrile derivative and an α-amino acid can be obtained in high yields.

21 Claims, No Drawings

PROCESSES FOR PRODUCING α-AMINONITRILE DERIVATIVES AND α-AMINO ACIDS

FIELD OF THE INVENTION

The present invention relates to processes for producing an α-aminonitrile derivative and an α-amino acid, or salts thereof from an oxime ester compound and a cyanogenation agent, or from an enol ester compound, an oxime compound and a cyanogenation agent.

BACKGROUND OF THE INVENTION

As a process for producing an α-amino acid, there has been known a process which comprises treating an aldehyde or a ketone with an alkali cyanide and ammonium chloride (or ammonia) to produce the corresponding α-aminonitrile (Strecker synthesis), and hydrolyzing the obtained α-aminonitrile by concentrated hydrochloric acid or the like.

Moreover, there have been known another processes for producing α-amino acids, such as a process which comprises aminating an α-halo acid, an acylaminomalonic acid ester process, a process which comprises reducing and aminating an α-keto acid, and azlactone synthesis (a process which comprises reducing a substituted unsaturated azlactone, obtainable by reacting an aldehyde and an N-acylglycine with sodium acetate in acetic anhydride, by red phosphorus and hydrogen iodide in glacial acetic acid).

These processes, however, are not necessarily satisfactory in view of yield and applicability.

SUMMARY OF THE INVENTION

It is, therefore, an object of the present invention to provide processes for producing α-aminonitrile derivatives and α-amino acids, or salts thereof in high yield.

The inventors of the present invention did intensive investigation, and found that the reaction of an oxime ester compound with a cyanogenation agent, or of an oxime compound with an enol ester compound and a cyanogenation agent in the presence of a metal catalyst provides the corresponding α-aminonitrile derivative in high yield even under mild conditions.

That is to say, the present invention provides a process for producing an α-aminonitrile derivative, which comprises, in the presence of a metal catalyst, reacting an oxime ester compound shown by the formula (1):

$$R^1-\underset{\underset{}{\overset{\overset{O}{\|}}{C}}}{}-O-N=C\underset{R^3}{\overset{R^2}{\diagup}} \quad (1)$$

wherein $R^1$, $R^2$, and $R^3$ may be the same or different from each other and each represents a non-reactive atom or a non-reactive organic group; and $R^2$ and $R^3$, together with the adjacent carbon atom, may bond together to form a ring with a cyanogenation agent
to form an aminonitrile derivative shown by the formula (2):

$$R^1-\underset{\underset{}{\overset{\overset{O}{\|}}{C}}}{}-O-\underset{\underset{R^3}{|}}{\overset{R^4}{|}}{N}-\underset{\underset{R^3}{|}}{\overset{CN}{|}}{C}-R^2 \quad (2)$$

wherein $R^4$ represents a cyano group-eliminated residue of the cyanogenation agent, or hydrogen atom; and $R^1$, $R^2$, and $R^3$ have the same meanings as defined above.

The present invention also provides a process for producing an α-aminonitrile derivative, which comprises, in the presence of a meatl catalyst, reacting an enol ester compound shown by the formula (3):

$$R^1-\underset{\underset{}{\overset{\overset{O}{\|}}{C}}}{}-O-\underset{\underset{}{\overset{R^5}{|}}}{C}=C\underset{R^7}{\overset{R^6}{\diagup}} \quad (3)$$

wherein $R^1$, $R^5$, $R^6$, and $R^7$ are the same or different from each other and each represents a non-reactive atom or a non-reactive organic group; and $R^5$, $R^6$, and $R^7$, together with one or two adjacent carbon atoms, may bond together to form a ring with an oxime compound shown by the formula (4):

$$HO-N=C\underset{R^3}{\overset{R^2}{\diagup}} \quad (4)$$

wherein $R^2$ and $R^3$ are the same or different from each other and each represents a non-reactive atom or a non-reactive organic group; and $R^2$ and $R^3$, together with the adjacent carbon atom, may bond together to form a ring and a cyanogenation agent
to form an α-aminonitrile derivative shown by the above formula (2).

In the formulae, $R^1$ may be selected from, e.g., hydrogen atom, $C_{1-10}$alkyl groups, $C_{2-10}$alkenyl groups, $C_{3-10}$cycloalkyl groups and $C_{6-10}$aryl groups. $R^2$ and $R^3$ may be selected from $C_{1-10}$alkyl groups, $C_{3-10}$cycloalkyl groups and $C_{6-10}$aryl groups. $R^2$ and $R^3$, together with the adjacent carbon atom, may form a 3 to 20-membered cycloalkane ring. $R^5$, $R^6$, and $R^7$ may be selected from, e.g., hydrogen atom, $C_{1-10}$alkyl groups, $C_{3-10}$cycloalkyl groups and $C_{6-10}$aryl groups. Preferably, $R^5$, $R^6$, and $R^7$ are preferably hydrogen atoms or $C_{1-3}$alkyl groups. As the cyanogenation agent, hydrogen cyanide, metal cyanides, cyanohydrin compounds, acyl cyanides and the like may be employed.

The present invention further provides a process for producing an α-amino acid shown by the formula (5):

$$H_2N-\underset{\underset{R^3}{|}}{\overset{CO_2H}{|}}{C}-R^2 \quad (5)$$

wherein $R^2$ and $R^3$ have the same meanings as defined above
or a salt thereof which comprises hydrolyzing an α-aminonitrile derivative produced according to the above process and shown by the above formula (2).

DETAILED DESCRIPTION OF THE INVENTION

[Metal Catalyst]

The metal catalyst includes simple substances and compounds of various metal elements, and may be used singly or as a combination thereof. As the metal elements, there may be exemplified the group 2A elements of the Periodic Table of Elements (e.g., magnesium Mg, calcium Ca, strontium Sr, barium Ba), transition metal elements, and the group 3B elements of the Periodic Table of Elements (e.g., boron B, aluminum Al). In the present specification, boron B is also included as a metal element.

As the transition metal elements, there may be exemplified the group 3A elements [rare earth metal elements (e.g., scandium Sc, yttrium Y, lanthanoid-series elements (lanthanum La, cerium Ce, praseodymium Pr, neodymium Nd, promethium Pm, samarium Sm, europium Eu, gadolinium Gd, terbium Tb, dysprosium Dy, holmium Ho, erbium Er, thulium Tm, ytterbium Yb, lutetium Lu), actinoid-series elements (e.g., actinium Ac)], the group 4A elements (e.g., titanium Ti, zirconium Zr, hafnium Hf), the group 5A elements (e.g., vanadium V, niobium Nb, tantalum Ta), the group 6A elements (e..g, chromium Cr, molybdenum Mo, tungsten W), the group 7A elements (e.g., manganese Mn, technetium Tc, rhenium Re), the group 8 elements (e.g., iron Fe, ruthenium Ru, osmium Os, cobalt Co, rhodium Rh, iridium Ir, nickel Ni, palladium Pd, platinum Pt), the group 1B elements (e.g., copper Cu, silver Ag, gold Au), and the group 2B elements (e.g., zinc Zn, cadmium Cd) of the Periodic Table of Elements.

Preferred elements as a component of the metal catalyst include transition metal elements (e.g., rare earth metal elements such as lanthanoid-series elements, the group 3A elements such as actinoid-series elements, the group 4A elements, the group 5A elements, the group 6A elements, the group 7A elements, the group 8 elements, the group 1B elements, the group 2B elements of the Periodic Table of Elements) and the group 3B elements of the Periodic Table of Elements.

Compounds comprising a metal element include hydroxides, metal oxides (e.g., double oxides or oxygen acids, or salts thereof), organic acid salts, inorganic acid salts, halides, coordination compounds (complex) containing any of the metal elements mentioned above, and polyacids (e.g., heteropolyacids and isopolyacids), or salts thereof. As for the metal compounds, the valence of their elements is not particularly restricted, and may be about 2 to 6.

As the hydroxides, there may be exemplified $Sm(OH)_2$, $Sm(OH)_3$, $Mn(OH)_2$, $MnO(OH)$, $Fe(OH)_2$, $Fe(OH)_3$, and other corresponding metal hydroxides. As the metal oxides, there may be exemplified $SmO_2$, $SmO_3$, $TiO_2$, $ZrO_2$, $V_2O_3$, $V_2O_5$, $CrO$, $Cr_2O_3$, $MoO_3$, $MnO$, $Mn_3O_4$, $Mn_2O_3$, $MnO_2$, $Mn_2O_7$, $FeO$, $Fe_2O_3$, $Fe_3O_4$, $RuO_2$, $RuO_4$, $CoO$, $CoO_2$, $Co_2O_3$, $RhO_2$, $Rh_2O_3$, $Cu_2O_3$, and other corresponding metal oxides. As the double oxides or oxygen acids, or salts thereof, there may be exemplified $MnAl_2O_4$, $MnTiO_3$, $LaMnO_3$, $K_2Mn_2O_5$, $CaO.xMnO_2(x=0.5, 1, 2, 3, 5)$, manganates [e.g., manganates (V) such as $Na_3MnO_4$ and $Ba_3[MnO_4]_2$; manganates (VI) such as $K_2MnO_4$, $Na_2MnO_4$, and $BaMnO_4$; and permanganates such as $KMnO_4$, $NaMnO_4$, $LiMnO_4$, $NH_4MnO_4$, $CsMnO_4$, $AgMnO_4$, $Ca(MnO_4)_2$, $Zn(MnO_4)_2$, $Ba(MnO_4)_2$, $Mg(MnO_4)_2$, and $Cd(MnO_4)_2$; molybdic acid; tungstic acid; and other corresponding metal double oxides or oxygen acids, or salts thereof.

As the organic acid salts, there may be exemplified salts of organic acids such as organic carboxylic acid (e.g., monocarboxylic acids such as formic acid, acetic acid, trichloroacetic acid, trifluoroacetic acid, propionic acid, butyric acid, valeric acid, naphthenic acid, and stearic acid; polycarboxylic acids such as oxalic acid and maleic acid); hydroxycarboxylic acids (e.g., glycolic acid, lactic acid, malic acid, tartaric acid, citric acid), thiocyanic acid, sulfonic acids (e.g., alkylsulfonic acids such as methanesulfonic acid, trichloromethanesulfonic acid, trifluoromethanesulfonic acid, and ethanesulfonic acid; arylsulfonic acids such as benzenesulfonic acid and p-toluenesulfonic acid). As the inorganic acid salts, there may be exemplified nitrates, sulfates, phosphates, carbonates, and perchlorates. Concrete examples of the organic acid salts or inorgnaic acid salts are samarium (II) acetate, samarium (III) acetate, cobalt acetate, manganese acetate, cobalt propionate, manganese propionate, cobalt naphthenate, manganese naphthenate, cobalt stearate, manganese stearate, manganese thiocyanate, samarium (II) trichloroacetate, samarium (III) trichloroacetate, samarium (II) trifluoroacetate, samarium (III) trifluoroacetate, samarium (II) trifluoromethanesulfonate (i.e., samarium (II) triflate), samarium (III) trifluoromethanesulfonate (i.e., samarium (III) triflate), samarium (II) nitrate, cobalt nitrate, iron nitrate, manganese nitrate, nickel nitrate, copper nitrate, samarium (II) sulfate, cobalt sulfate, iron sulfate, manganese sulfate, samarium (II) phosphate, cobalt phosphate, iron phosphate, manganese phosphate, samarium (II) carbonate, iron carbonate, manganese carbonate, iron perchlorate, and other corresponding metal organic acid salts or inorganic acid salts.

The halides include fluorides, chlorides, bromides and iodides. There may be mentioned, for example, halides such as chlorides [e.g., $SmCl_2$, $SmCl_3$, $TiCl_2$, $TiCl_4$, $ZrCl_2$, $ZrOCl_2$, $VCl_3$, $VOCl_2$, $MoCl_3$, $MnCl_2$, $MnCl_3$, $FeCl_2$, $FeCl_3$, $RuCl_3$, $CoCl_2$, $RhCl_2$, $RhCl_3$, $NiCl_2$, $PdCl_2$, $PtCl_2$, $CuCl$, $CuCl_2$, $AlCl_3$], the corresponding fluorides, bromides and iodides (e.g., $SmF_2$, $SmF_3$, $SmBr_2$, $SmBr_3$, $SmI_2$, $SmI_3$, $MnF_2$, $MnBr_2$, $MnF_3$, $FeF_2$, $FeF_3$, $FeBr_2$, $FeBr_3$, $FeI_2$, $CuBr$, $CuBr_2$), double halides such as $M^1MnCl_3$, $M^1{}_2MnCl_4$, $M^1{}_2MnCl_5$, $M^1{}_2MnCl_6$ ($M^1$ indicates a monovalent metal), and other corresponding metal halides.

As ligands forming the complexes, there may be exemplified hydroxo (OH), alkoxy groups such as methoxy, ethoxy, propoxy, and butoxy groups; acyl groups such as acetyl, and propionyl groups; alkoxycarbonyl groups such as methoxycarbonyl (acetato) and ethoxycarbonyl groups; acetylacetonato, cyclopentadienyl, $C_{1-4}$alkyl-substituted dicyclopentadienyls (e.g., pentamethylcyclopentadienyl); halogen atoms such as chlorine and bromine; CO; CN; oxygen atom; $H_2O$ (aquo); phosphorous compounds such as phosphines (e.g., triarylphosphines such as triphenylphosphine); oxygen-containing compounds such as tetrahydrofuran; and nitrogen-containing compounds such as $NH_3$ (ammine), NO, $NO_2$ (nitro), $NO_3$(nitrato), ethylenediamine, diethylenetriamine, pyridine, and phenanthroline. In the complexes or complex salts, the species of ligands may be the same or different from each other, and one or more than two species of ligands may be coordinated therein.

In the complexes, e.g., OH group, alkoxy groups, acyl groups, alkoxycarbonyl groups, acetylacetonato, cyclopentadienyl, $C_{1-2}$alkyl-substituted cyclopentadienyls, halogen atoms, CO, CN, $H_2O$ (aquo), phosphorous compounds such as triphenylphosphine, oxygen-containing compounds such as tetrahydrofuran (THF), or nitrogen-containing compounds inclusive of $NH_3$, $NO_2$ and $NO_3$ are usually preferred. As the complexes, there may be exemplified an acetylacetonato complex (e.g., acetylacetonato complexes of e.g., Ce, Ti, Zr, V, Cr, Mo, Mn, Fe, Ru, Co, Ni, Cu, or Zn; titanylacetylacetonato complex TiO(AA)$_2$; zirconylacetylacetonato complex ZrO(AA)$_2$; vanadylacetylacetonato complex VO(AA)$_2$; diacetylacetonatosamarium (II); triacetylacetonatosamarium (III), cyano complexes (e.g., hexacyanomanganate (I), hexacyanocuprate (II)), carbonyl complexes and cyclopentadienyl complexes (e.g., samallocene-type complexes such as dicyclopentadienylsamarium (II), tricyclopentadienylsamarium (III), dipentamethylcyclopentadienylsamarium (II), and tripentamethylcyclopentadienylsamarium (III); tricarbonylcyclopentadienylmanganese (I), biscyclopentadienylmanganese (II), biscyclopentadienyliron(II), Fe(CO)$_5$, Fe$_2$(CO)$_9$, Fe$_3$(CO)$_{12}$); nitrosyl compounds (e.g., Fe(NO)$_4$, Fe(CO)$_2$, (NO)$_2$); thiocyanato complexes (e.g., thiocyanatocobalt, thiocyanatomanganese, thiocyanatoiron), acety complexes (e.g., zirconyl acetate ZrO(OAc)$_2$, titanyl acetate TiO(OAc)$_2$, vanadyl acetate VO(OAc)$_2$), and other corresponding metal complexes.

A polyacid (e.g., isopolyacid and heteropolyacid) is usually at least one of, e.g., the group 5A elements or the group 6A elements of the Periodic Table of Elements, e.g., V (vanadic acid), Mo (molybdic acid) and W (tungstic acid). The central atom is not particularly restricted, and may be, e.g., Cu, Be, B, Al, Si, Ge, Sn, Ti, Th, N, P, As, Sb, V, Nb, Ta, Cr, Mo, W, S, Se, Te, Mn, I, Fe, Co, Ni, Rh, Os, Ir, or Pt. As concrete examples of the heteropolyacids or salts thereof, there may be mentioned phosphomolybdic acid, phosphotungstic acid, silicomolybdic acid, silicotungstic acid, cobaltmolybdic acid, cobalttungstic acid, molybdenumtungstic acid, manganesemolybdic acid, manganesetungstic acid, manganesemolybdenumtungstic acid, vanadomolybdophosphoric acid, phosphovanadomolybdic acid, manganesevanadiummolybdic acid, manganesevanadomolybdophosphoric acid, and salts thereof.

Further, as boron compounds, there may be exemplified boric acids (e.g., orthoboric acid, methaboric acid, tetraboric acid); borates (e.g., nickel borate, magnesium borate, manganese borate); boron oxides such as B$_2$O$_3$, nitrogen-containing compounds such as borazane, borazen, borazine, and boron amide; halides such as BF$_3$, BCl$_3$, and tetrafluoroborate; and boric esters (e.g., methyl borate, phenyl borate).

The metal catalyst may be a homogeneous or heterogeneous system. Further, the catalyst may be a solid catalyst in which a catalytic component is supported on a carrier. Porous carriers such as acitivated carbon, zeolites, silica, silica-alumina, bentonite are usually employed as the carrier. The amount of the catalytic component supported on the carrier is about 0.1 to 50 parts by weight, preferably about 0.5 to 30 parts by weight, and more preferably about 1 to 20 parts by weight, relative to 100 parts by weight of the carrier.

The catalyst is useful in producing an α-aminonitrile derivative shown by the above formula (2) by reacting an oxime ester compound shown by the formula (1) with a cyanogenation agent, or by reacting an enol ester compound shown by the furmula (3) with an oxime compound shown by the formula (4) and a cyanogenation agent.

[Oxime Ester Compound]

In an oxime ester compound shown by the formula (1), each of $R^1$, $R^2$, and $R^3$ represents a non-reactive atom or a non-reactive organic group.

The non-reactive atom or non-reactive organic group includes, e.g., hydrogen atom, halogen atoms, alkyl groups, alkenyl groups, alkynyl groups, aryl groups, cycloalkyl groups, and heterocyclic groups.

The halogen atoms include iodine, bromine, chlorine, and fluorine. The alkyl groups include linear or branched chain alkyl groups having about 1 to 20 carbon atoms (preferably, alkyl groups having about 1 to 10 carbon atoms), such as methyl, ethyl, propyl, isopropyl, butyl, isobutyl, sec-butyl, t-butyl, pentyl, hexyl, heptyl, octyl, decyl, undecyl, dodecyl, tetradecyl, and octadecyl group. Preferred alkyl groups are, e.g., lower alkyl groups having about 1 to 6 carbon atoms, particularly about 1 to 4 carbon atoms.

The alkenyl groups include alkenyl groups having about 2 to 20 carbon atoms (preferably alkenyl groups having about 2 to 10 carbon atoms, particularly about 2 to 6 carbon atoms), such as vinyl, propenyl, 2-propenyl, butenyl, pentenyl, octenyl, and dodecyl group.

The alkynyl groups include alkynyl groups having about 2 to 20 carbon atoms (preferably alkynyl groups having about 2 to 10 carbon atoms, particularly about 2 to 6 carbon atoms), such as ethynyl, propynyl, and octhynyl group.

The aryl groups include aryl groups having about 6 to 14 carbon atoms, such as phenyl group and naphthyl group. Cycloalkyl groups include cycloalkyl groups having about 3 to 10 carbon atoms, such as cyclopentyl, cyclohexyl, cycloheptyl, and cyclooctyl group.

Heterocycles corresponding to the heterocyclic groups include hyterocycles containing an oxygen atom as a heteroatom (e.g., 5-membered rings such as furan, oxazole, isooxazole, and tetrahydrofuran; 6-membered rings such as pyran; fused or condensed rings such as benzofuran, isobenzofuran, dibenzofuran, xanthone, xanthene, chroman, isochroman, and chromene), heterocycles containing a sulfur atom as a heteroatom (e.g., thiophene, thiazole, isothiazole, thiadiazole, benzothiophene), heterocycles containing a nitrogen atom as a heteroatom (e.g., 5-membered rings such as pyrrole, pyrazole, imidazole, triazole, and pyrrolidine; 6-membered rings such as pyridine, pyridazine, pyrimidine, pyrazine, piperidine, and morpholine; fused or condensed rings such as indole, indolene, isoindole, indazole, indoline, isoindoline, quinoline, isoquinoline, quinolinequinoline, quinoxaline, quinazoline, phthalazine, purine, carbazole, acridine, naphthoquinoline, phenanthrodine, phenanthroline, naphthyridine, benzoquinoline, phenoxazine, phthalocyanine, and anthracyanine.

As a ring formed by $R^2$ and $R^3$ bound together with the adjacent carbon atom, there may be mentioned, e.g., cycloalkane rings or cycloalkene rings such as cyclopropane ring, cyclobutane ring, cyclopentane ring, cyclohexane ring, cyclohexene ring, cycloheptane ring, cyclooctane ring, cyclodecane ring and cyclododecane ring; and non-aromatic heterocycles containing 1 to 3 heteroatoms such as oxygen atom, sulfur atom and nitrogen atom. These are, e.g., about 3 to 20-membered, preferably about 3 to 16-membered, more preferably about 3 to 12-membered, and particularly about 5 to 10-membered rings.

The alkyl groups, aryl groups, cycloalkyl groups, heterocyclic groups represented by $R^1$, $R^2$, and $R^3$, and rings formed by $R^2$ and $R^3$ bound together with the adjacent carbon atom may have a substituent. As the substituent, there may be exemplified hydroxyl group, mercapto group, carboxyl group, substituted-oxy groups (e.g., alkoxy, aryloxy group), substituted-thio groups (e.g., alkylthio group, arylthio group), substituted-oxycarbonyl groups (e.g., alkoxycarbonyl group, aryloxycarbonyl group), oxo group, carbamoyl group, substituted-carbamoyl group, cyano group, nitro group, amino group, substituted-amino groups, sulfo group, aromatic hydrocarbon groups, heterocyclic groups, halogen atoms, alkyl groups, alkenyl groups, alkynyl groups, and cycloalkyl groups.

Included as preferable $R^1$ are hydrogen atom, $C_{1-10}$alkyl groups (e.g., $C_{1-6}$alkyl groups, particularly $C_{1-4}$alkyl groups), $C_{2-10}$alkenyl groups (e.g., $C_{2-6}$alkenyl groups), $C_{6-10}$aryl groups (e.g., phenyl group), and $C_{3-10}$cycloalkyl groups (e.g., $C_{5-8}$cycloalkyl groups). Among them, e.g., hydrogen atom, methyl group, ethyl group, vinyl group, 2-propenyl group, and phenyl group are preferred as R1.

Included as preferable $R^2$ and $R^3$ are, e.g., hydrogen atom, $C_{1-10}$alkyl groups (e.g., $C_{1-6}$alkyl groups), $C_{6-10}$aryl groups (e.g., phenyl group), and $C_{3-10}$cycloalkyl groups (e.g., $C_{5-8}$cycloalkyl groups). Moreover, the formation of a ring (e.g., 3 to 20-membered ring, preferably 3 to 16-membered ring, more preferably 3 to 12-membered ring, and particularly 5 to 10-membered ring) composed of $R^2$ and $R^3$ bound together and the adjacent carbon atom is also preferable. By varying $R^2$ and $R^3$, various corresponding α-aminonitrile derivatives can be produced.

An oxime ester compound shown by the above formula (1) can be obtained by, e.g., reacting an enol ester compound shown by the formula (3) with an oxime compound shown by the formula (4) in the presence of the metal catalyst (e.g., compounds containing a Group 3 element of the Periodic Table of Elements, such as samarium compounds).

$R^1$ in the formula (3) is the same as $R^1$ in the formula (1). As non-reactive organic groups and preferred organic groups represented by $R^5$, $R^6$, and $R^7$, those exemplified as non-reactive organic groups and preferred organic groups represented by $R^2$ and $R^3$ are mentioned. Moreover, as a ring formed by $R^5$, $R^6$ and $R^7$ bound together with the adjacent one or two carbon atoms, those exemplified as rings formed of $R^2$, $R^3$, and the adjacent carbon atom are mentioned. As $R^5$, $R^6$ and $R^7$, hydrogen atom or $C_{1-3}$alkyl groups are preferable. Particularly preferred as $R^5$ are hydrogen atom and methyl group. As $R^6$ and $R^7$, hydrogen atom is particularly preferred.

Preferable compounds shown by the formula (3) are vinyl formate, vinyl acetate, vinyl propionate, isopropenyl formate, isopropenyl acetate, and isopropenyl propionate.

As an oxime compound shown by the formula (4), compounds corresponding to an oxime ester compound shown by the formula (1) are employed. As an oxime compound (4), there may be exemplified aliphatic oximes such as 2-hexanone oxime; alicyclic oximes such as cyclohexanone oxime and cyclopentanone oxime; aromatic oximes such as acetophenone oxime, benzophenone oxime, and benzyl dioxime.

The reaction of a compound shown by the formula (3) with a compound shown by the formula (4) is usually conducted in a solvent. As the solvent, there may be exemplified aromatic hydrocarbons such as benzene, toluene, xylene, and ethylbenzene; hydrocarbon halides such as carbon tetrachloride, chloroform, dichloromethane, and 1,2-dichloroethane; aliphatic hydrocarbons such as pentane, hexane, heptane, and octane; alicyclic hydrocarbons such as cyclohexane and methylcyclohexane; esters such as methyl acetate, ethyl acetate, isopropyl acetate, butyl acetate, amyl acetate, cellosolve acetate, and ethyl propionate; ethers such as diethyl ether, dibutyl ether, dioxane, and tetrahydrofuran; ketones such as acetone and methyl ethyl ketone; and non-protonic polar solvents such as acetonitrile, N,N-dimethylformamide, and dimethyl sulfoxide.

In the above reaction, the ratio of a compound shown by the formula (3) to a compound shown by the formula (4) is, e.g., the former/the latter (molar ratio)=about 1/5 to 5/1, preferably about 1/2 to 2/1, and more preferably about 1/1.5 to 1.5/1. Moreover, the amount of the metal catalyst is, relative to 1 mole of a compound shown by the formula (4), about 0.001 to 1 mole, preferably about 0.01 to 0.5 mole, and more preferably about 0.05 to 0.2 mole. The reaction temperature may be, e.g., about 0 to 100° C., preferably about 10 to 60° C., and more preferably about 10 to 40° C.

After the completion of the reaction, a compound shown by the formula (1) is separated and purified by a conventional separation and purification method such as filtration, concentration, extraction, crystallization, recrystallization, and column chromatography.

[Cyanogenation Agent]

As the cyanogenation agent, there may be employed a conventional cyanogenation agent used for cyanogenation reaction. For example, there may be mentioned hydrogen cyanide, metal cyanides, cyanohydrin compounds, acyl cyanides, and cyanogen halides. The metal cyanides include, e.g., cyanides of alkaline metals, such as sodium cyanide and potassium cyanide; cyanides of alkaline earth metals, such as calcium cyanide; and cyanides of transition metals, such as copper cyanide. The cyanohydrin compounds include a wide range of α-cyanohydrin compounds corresponding to aliphatic, alicyclic, or aromatic aldehydes or ketones. As typical examples of the α-cyanohydrin compounds, there may be mentioned aliphatic α-cyanohydrins such as hydroxyacetonitrile, lactonitrile, acetone cyanohydrin, 2-hydroxybutanenitrile, 2-hydroxy-4-methylbutanenitrile, 2-hydroxy-3-methylbutanenitrile, 2-hydroxy-3-butenenitrile, 2-hydroxypentanenitrile, 2-hydroxyhexanenitrile, and 2-hydroxyoctanenitrile; alicyclid α-cyanohydrins such as 2-hydroxycyclohexaneacetonitrile and cyclopentanone cyanohydrin; and aromatic α-cyanohydrins such as mandelonitrile and 2-hydroxy-3-phenylbutanenitrile. The acyl cyanides include aliphatic acyl cyanides such as acetyl cyanide and propionyl cyanide; and aromatic acyl cyanides such as benzoyl cyanide. The cyanogen halogenides include chlorocyanogen and bromocyanogen.

Preferred cyanogenation agents are, e.g., hydrogen cyanide, metal cyanides, cyanohydrin compounds, andacylcyanides. Amongthem, hydrogencyanide, cyanides of alkalinemetals, and cyanohydrin compounds (especially, aliphatic α-cyanohydrins having about 3 to 8 carbon atoms) are preferred.

[Reaction of a Compound Shown by the Formula (1) with a Cyanogenation Agent]

The reaction of a compound shown by the formula (1) with a cyanogenation agent may be conducted in the absence of a solvent, but usually conducted in a solvent. As the solvent, those exemplified as the solvent for the reaction of a compound shown by the formula (3) with a compound shown by the formula (4) may be employed.

The amount of the cyanogenation agent is, relative to 1 mole of a compound shown by the formula (1), e.g., not less than 0.8 mole (e.g., about 0.8 to 5 mole), preferably about 0.8 to 3 mole, and more preferably about 0.9 to 1.5 mole.

The amount of the metal catalyst (e.g., a compound containing a Group 3 element of the Periodic Table of Elements) is, relative to 1 mole of a compound shown by the formula (1), e.g., about 0.001 to 1 mole, preferably about 0.01 to 0.5 mole, and more preferably about 0.05 to 0.2 mole. The reaction temperature is, e.g., about 0 to 100° C., preferably about 10 to 60° C., and more preferably about 10 to 40° C.

According to the above reaction, an α-aminoniritle derivative shown by the formula (2) is formed, which corresponds to an oxime ester compound shown by the formula (1). In the formula (2), $R^4$ represents a cyanogen group-eliminated residue of the cyanogenation agent used, or hydrogen atom, and it depends on what is employed as the cyanogenation agent. For example, when employing, as the cyanogenation agent, hydrogen cyanide, a metal cyanide, an acyl cyanide, or a cyanogen halide, $R^4$ usually represents a cyano group-eliminated residue of the cyanogenation agent used (in other words, a residue of the cyanogenation agent, from which a cyano group is eliminated) (i.e., represents hydrogen atom, a metal atom, an acyl group, a halogen atom, respectively). When employing a cyanohydrin compound as the cyanogenation agent, $R^4$ represents hydrogen atom. Even if, e.g., a metal cyanide is employed as the cyanogenation agent, the presence of a protonic compound (e.g., water, alcohols) in the system or addition of a protonic compound after the reaction enables the conversion of $R^4$ to hydrogen atom.

Further, in this reaction, a compound shown by the formula (3) may be present in the system. In this case, the amount of a compound shown by the formula (3) is, relative to 1 mole of a compound shown by the formula (1), e.g., about 0.001 to 2 mole, and preferably about 0.01 to 1.8 mole (e.g., about 0.5 to 1.5 mole).

The reaction may be carried out in a conventional manner such as batch system, semi-batch system, and continuous system. After the completion of the reaction, a compound shown by the formula (2) can be separated and purified by a conventional separation or purification method, e.g., filtration, concentration, extraction, crystallization, recrystallization, column chromatography, or a combination of such methods.

[Reaction of a Compound Shown by the Formula (3) with a Compound Shown by the Formula (4) and a Cyanogenation Agent]

An α-aminonitrile derivative shown by the formula (2) can be obtained also by, in the presence of the metal catalyst, reacting a compound shown by the formula (3) with a compound shown by the formula (4) and the cyanogenation agent.

This reaction, as well as the reaction described above, may be conducted either in the presence or absence of a solvent. As the solvent, solvents similar to those exemplified in connection with the reaction of a compound shown by the formula (1) with a cyanogenation reaction can be employed. As the metal catalyst employed in this process, compounds containing a Group 3 element of the Periodic Table of Elements, such as samarium compounds, are preferable.

In this reaction, the ratio of a compound shown by the formula (3) to a compound shown by the formula (4) is, e.g., the former/the latter (molar ratio)=about 1/5 to 5/1, preferably about 1/2 to 2/1, and more preferably about 1/1.5 to 1.5 to 1. The amount of the cyanogenation agent is, relative to 1 mole of a compound shown by the formula (4), e.g., not less than 0.8 mole (e.g., about 0.8 to 5 mole), preferably about 0.8 to 3 mole, and more preferably about 0.9 to 1.5 mole. The amount of the metal catalyst is, relative to 1 mole of a compound shown by the formula (4), e.g., about 0.001 to 1 mole, preferably about 0.01 to 0.5 mole, and more preferably about 0.05 to 0.2 mole. The reaction temperature is, e.g., about 0 to 100° C., preferably about 10 to 60° C., and more preferably about 10 to 40° C.

The reaction may be carried out in a conventional manner such as batch system, semi-batch system, and continuous system. After the completion of the reaction, a compound shown by the formula (2) may be separated and purified by any of the separation/purification methods exemplified above.

According to the process for producing an α-aminonitrile derivative of the present invention, an α-aminonitrile derivative which is a precursor of an amino acid can be produced in good yield.

[The Production of α-amino Acids or Salts Thereof]

An α-amino acid or a salt thereof can be obtained by hydrolyzing the α-aminonitrile derivative shown by the formula (2) obtained according to the above process.

The hydrolysis may be conducted in a conventional manner, e.g., acid hydrolysis method, alkali hydrolysis method.

As acids that may be employed for acid hydrolysis, there may be exemplified inorganic acids such as hydrochloric acid, sulfuric acid, nitric acid, and phosphoric acid; and sulfonic acids such as methanesulfonic acid, ethanesulfonic acid, benzenesulfonic acid, and p-toluenesulfonic acid. The amount of an acid may be a catalytic amount. For example, the amount of an acid is, relative to 1 mole of an α-aminonitrile derivative shown by the formula (2), about 0.00001 to 1 mole, preferably about 0.00005 to 0.5 mole, and more preferably about 0.0001 to 0.1 mole.

The amount of water is not less than 1 mole relative to 1 mole of a compound shown by the formula (2), and may be suitably selected within the range of about 1 to 100 mole. The hydrolysis may be conducted in the presence of an organic solvent, provided that the reaction is not adversely affected. As the organic solvent, the solvents exemplified above may be mentioned. The reaction temperature is, e.g., about 0 to 150° C., preferably about 10 to 110° C., and more preferably about 40 to 100° C.

Usually, by acid hydrolysis, a free α-amino acid or an acid salt of an α-amino acid is formed. Such products can be converted into basic salts of α-amino acids by a conventional method.

The alkali hydrolysis is carried out in the presence of a base. As the base, there may be exemplified hydroxides of alkaline metals, such as lithium hydroxide, sodium hydroxide, and potassium hydroxide; hydroxides of alkaline earth matals, such as magnesium hydroxide, calcium hydroxide, and barium hydroxide; carbonates of alkaline metals, such as sodium carbonate and potassium carbonate; carbonates of alkaline earth metals such as magnesium carbonate; and hydrogencarbonates of alkaline metals, such as sodium hydrogencarbonate and potassium hydrogencarbonate.

The amount of the basis is, relative to 1 mole of a compound shown by the formula (2), not less than 1 mole, e.g., about 1 to 10 mole, preferably about 1 to 5 mole, and more preferably about 2 to 3 mole. The amount of water is similar to those exemplified in the paragraphs referring to acid hydrolysis, and the reaction may be conducted in the presence of any of the aforementioned organic solvents or alchols (e.g., methanol, ethanol). The reaction temperature is, e.g., about 0 to 150° C., and preferably about 10 to 110° C.

Usually, the alkaline hydrolysis provides the corresponding basic salt of an α-amino acid. The basic salt of the α-amino acid can be converted to a free α-amino acid or an acid salt thereof by a conventional method.

The hydrolysis reaction may be conducted in a conventional manner such as batch system, semi-batch system, and continuous system. After the completion of the reaction, the pH is adjusted, if need be, and then the reaction product is easily separated and purified by a conventional separation method, e.g., filtration, concentration, distillation, extraction, crystallization, recrystallization, column chromatography, and a combination of these methods.

INDUSTRIAL APPLICABILITY

According to the present invention, an α-aminonitrile derivative can be obtained from an oxime compound or an oxime ester compound in good yield. Moreover, by hydrolyzing the α-aminonitrile derivative, the corresponding α-amino acid or a salt thereof can be produced in good yield.

EXAMPLES

The following examples are intended to describe the present invention in further detail and should by no means be interpreted as defining the scope of the invention.

Preparation Example 1

A mixture of 2.3 g (20 mmole) of cyclohexanone oxime, 2.0 g (20 mmole) of isopropenyl acetate, 0.9 g (2 mmole) of di($\eta^5$-pentamethylcyclopentadienyl)samarium [Cp*$_2$Sm(THF)$_2$], and 20 ml of toluene was stirred at room temperature for one hour, and the precipitated crystals were filtered. 3.1 g of acetyloxyiminocyclohexane (O-acetylcyclohexanone oxime) (yield: 100%) was obtained.

Preparation Example 2

The same procedure as Preparation Example 1 was followed except for the use of 20 mmole of cyclopentanone oxime instead of cyclohexanone oxime. Acetyloxy iminocyclopentanone (O-acetylcyclopentanone oxime) was obtained (yield: 100%).

EXAMPLE 1

A mixture of 0.155 g (1 mmole) of acetyloxyiminocyclohexane obtained in the above Preparation Example 1, 0.085 g (1 mmole) of acetone cyanohydrin, 0.045 g (0.1 mmole) of di($\eta^5$-pentamethylcyclopentadienyl)samarium [Cp*$_2$Sm (THF)$_2$], and 1 ml of toluene was stirred at 25° C. for 3 hours. The analysis by gas chromatography revealed that 0.089 g of 1-acetyloxyamino-1-cyanocyclohexane (yield: 49%, acetyloxyiminocyclohexane basis) is formed in the reaction mixture. The conversion of acetyloxyiminocyclohexane was 74%, and cyclohexanone oxime was formed in a 9% yield.

By subjecting the reaction mixture to column chromatography, 1-acetyloxyamino-1-cyanocyclohexane was separated and purified, and each spectrum of $^1$H-NMR, $^{13}$C-NMR, IR, and MASS was measured.

$^1$H-NMR(CDCl$_3$)δ: 1.15–2.15(10H, m), 2.11(3H, s), 7.58 (1H, s)

$^{13}$C-MMR(CDCl$_3$)δ: 18.67, 21.73, 24.64, 32.92, 59.43, 119.89, 169.92

IR(cm$^{-1}$): 3852, 3750, 3648, 3207, 2950, 2885, 2363, 1740, 1540, 1507, 1456, 1375, 1248, 1010, 977, 931, 606

MS: 182(M$^+$), 135, 123, 113, 81, 67, 53, 43, 27

EXAMPLE 2

The same procedure as Example 1 was followed except that the mixture was stirred at 25° C. for 20 hours. And, as a result of the reaction, 0.084 g of 1-acetyloxyamino-1-cyanocyclohexane (yield: 46%, acetyloxy iminocyclohexane base) was formed in the reaction mixture. The conversion of acetyloxyiminocyclohexane was 84%, and cyclohexanone oxime was formed in a 21% yield.

EXAMPLE 3

The same procedure as Example 1 was followed except for the use of 0.17 g (2 mmole) of acetone cyanohydrin. As a result of the reaction, 0.089 g of 1-acetyloxyamino-1-cyanocyclohexane (yield: 49%, acetyloxy iminocyclohexane basis) was formed in the reaction mixture. The conversion of acetyloxyiminocyclohexane was 77%, and cyclohexanone oxime was formed in a 17% yield.

EXAMPLE 4

The same procedure as Example 1 was followed except that the use of 0.1 mmole of triisopropoxysamarium [Sm (O-i-Pr)$_3$] instead of di($\eta^5$-pentamethylcyclopentadienyl) samarium [Cp*$_2$Sm(THF)$_2$]. As a result of the reaction, 0.031 g of 1-acetyloxyamino-1-cyanocyclohexane (yield: 17%, acetyloxyiminocyclohexane basis) was formed in the reaction mixture. The conversion of acetyloxyiminocyclohexane was 80%, and cyclohexanone oxime was formed in a 30% yield.

EXAMPLE 5

The same procedure as Example 1 was followed except that the use of 0.1 mmole of aluminum chloride anhydride (AlCl$_3$) instead of di($\eta^5$-pentamethylcyclopentadienyl) samarium [Cp*$_2$Sm(THF)$_2$]. As a result of the reaction, 1-acetyloxyamino-1-cyanocyclohexane was obtained (yield: 82%). The conversion of acetyloxyiminocyclohexane was 89%.

EXAMPLE 6

The same procedure as Example 1 was followed except that the use of 0.1 mmole of zirconyl chloride (ZrOCl$_2$) instead of di($\eta$5-pentamethylcyclopentadienyl)samarium [CP*$_2$Sm(THF)$_2$]. As a result of the reaction, 1-acetyloxyamino-1-cyanocyclohexane (yield:73%) was obtained. The conversion of acetyloxyiminocyclohexane was 79%.

EXAMPLE 7

The same procedure as Example 1 was followed except for the use of 0.1 mmole of titanium tetrachloride (TiCl$_4$) instead of di($\eta^5$-pentamethylcyclopentadienyl)samarium [Cp*$_2$Sm(THF)$_2$]. As a result of the reaction, 1-acteylonyamino-1-cyanocyclohexane (yield: 72%) was obtained. The conversion of acetyloxyiminocyclohexane was 78%.

EXAMPLE 8

The same procedure as Example 1 was followed except for the use of 0.1 mmole of acetylacetonatozinc [Zn(AA)$_2$] instead of di($\eta^5$ -pentamethylcyclopentadienyl)samarium [Cp*$_2$Sm(THF)$_2$]. As a result of the reaction, 1-acetyloxyamino-1-cyanocyclohexane (yield: 64%) was obtained. The conversion of acetyloxyiminocyclohexane was 68%.

EXAMPLE 9

The same procedure as Example 1 was folloed except for the use of 0.1 mmole of copper chloride [Cu(Cl)$_2$] instead of di($\eta^5$-pentamethylcyclopentadienyl)samarium [Cp*$_2$Sm (THF)$_2$]. As a result of the reaction, 1-acetyloxyamino-1-cyanocylohexane (yield: 58%) was obtained. The conversion of acetyloxyiminocylohexane was 61%.

EXAMPLE 10

The same procedure as Example 1 was followed except for the use of 0.1 mmole of ferric chloride [Fe(Cl)$_3$] instead of di($\eta^5$-pentamethylcyclopentadienyl)samarium [Cp*$_2$Sm (THF)$_2$]. As a result of the reaction, 1-acetyoxyamino-1-cyanocyclohexane (yield: 57%) was obtained. The conversion of acetyloxyiminocyclohexane was 59%.

EXAMPLE 11

The same procedure as Example 1 was followed except for the use of 0.1 mmole of vanadyl chloride (VOCl$_2$) instead of di($\eta^5$-pentamethylcyclopentadienyl)samarium [Cp*$_2$Sm(THF)$_2$]. As a result of the reaction, 1-acetyloxyamino-1-cyanocyclohexane (yield: 72%) was obtained. The conversion of acetyloxyiminocyclohexane was 76%.

EXAMPLE 12

The same procedure as Example 1 was followed except for the use of 0.1 mmole of molybdenum chloride [Mo(Cl)$_3$] instead of di($\eta^5$-pentamethylcyclopentadienyl)samarium [Cp*$_2$Sm(THF)$_2$]. As a result of the reaction, 1-acetyloxyamino-1-cyanocylohexane (yield: 73%) was obtained. The conversion of acetyloxyiminocyclohexane was 74%.

EXAMPLE 13

The same procedure as Example 1 was followed except for the addition of 1 mmole of isopropenyl acetate to the reaction system. As a result of the reaction, 1-acetyloxyamino-1-cyanocyclohexane (yield: 56%) was obtained. The conversion of acetyloxyiminocyclohexane was 74%, and cyclohexanone oxime was formed in the reaction mixture in a 4% yield.

EXAMPLE 14

The same procedure as Example 1 was followed except for the use of 1 mmole of acetyloxyiminocyclopentane obtained in Preparation Example 2 instead of acetyloxyiminocyclohexane, and for the reaction temperature varied to 50° C. As a result of the reaction, 1-acetyloxyamino-1-cyanocyclopentane was obatained in a 46% yield.

IR(cm−1): 3850, 3740, 3650, 3200, 2950, 2360, 1750, 1540, 1450, 1250, 950

MS: 168(M+), 121, 109, 99, 67

EXAMPLE 15

A mixture of 0.115 g (1 mmole) of cyclohexanone oxime, 0.1 g (1 mmole) of isopropenyl acetate, 0.085 g (1 mmole) of acetone cyanohydrin, 0.045 g (0.1 mmole) of di($\eta^5$-pentamethylcyclopentadienyl)samarium [Cp*$_2$Sm(THF)$_2$], and 1 ml of toluene was stirred at 25° C. for 3 hours. 1-acetyloxyamino-1-cyanocyclohexane was formed in the reaction mixture in a 60% yield, and the conversion of cyclohexanone oxime was 72%.

EXAMPLE 16

A mixture of 10 mmole of 1-acetyloxyamino-1-cyanocyclohexane obtained in a manner similar to Example 1, 20 mmole of potassium hydroxide, 10 ml of water, and 10 ml of ethanol was stirred at 60° C. for 4 hours. The analysis of the reaction mixture by high performance liquid chromatography revealed the formation of 1-amino-1-cyclohexanecarboxylic acid in a 82% yield.

What is claimed is:

1. A process for producing an α-aminonitrile derivative, which comprises reacting, in the presence of a metal catalyst, (i) an oxime ester compound shown by the formula (1):

$$R^1-\underset{\underset{O}{\|}}{C}-O-N=C\underset{R^3}{\overset{R^2}{<}} \quad (1)$$

wherein $R^1$, $R^2$, and $R^3$ are the same or different from each other and each represents a non-reactive atom or a non-reactive organic group; and $R^2$ and $R^3$, together with the adjacent carbon atom, may bond together to form a ring (ii) with a cyanogenation agent having the formula $R^4$CN to form an α-aminonitrile derivative shown by the formula (2):

$$R^1-\underset{\underset{O}{\|}}{C}-O-N-\underset{\underset{R^3}{|}}{\overset{\overset{CN}{|}}{\underset{|}{C}}}-R^2 \quad (2)$$

wherein $R^4$ represents the residue $R^4$ of the cyanogenation agent $R^4$CN; and $R^1$, $R^2$, and $R^3$ have the same meanings as defined above and $R^4$CN comprises hydrogen cyanide, a metal cyanide, a cyanohydrin compound, an acyl cyanide, or a cyanogen halide.

2. A process for producing an α-aminonitrile derivative, which comprises reacting, in the presence of a metal catalyst, (i) an enol ester compound shown by the formula (3):

$$R^1-\underset{\underset{O}{\|}}{C}-O-\underset{\overset{R^5}{|}}{C}=C\underset{R^7}{\overset{R^6}{<}} \quad (3)$$

wherein $R^1$, $R^5$, $R^6$, and $R^7$ are the same or different from each other and each represents a non-reactive atom or a non-reactive organic group; and $R^5$, $R^6$ and $R^7$, together with one or two adjacent carbon atoms, may bond together to form a ring (ii) with an oxime compound shown by the formula (4):

$$HO-N=C\underset{R^3}{\overset{R^2}{<}} \quad (4)$$

(iii) and a cyanogenation agent having the formula $R^4$CN to form an α-aminonitrile derivative shown by the formula (2):

$$R^1-\underset{\underset{O}{\|}}{C}-O-N-\underset{\underset{R^3}{|}}{\overset{\overset{CN}{|}}{\underset{|}{C}}}-R^2 \quad (2)$$

wherein $R^4$ represents the residue $R^4$ of the cyanogenation agent $R^4$CN; and $R^1$, $R^2$, $R^3$ and $R^4$ have the same meanings as defined above.

3. A process for producing an α-aminonitrile derivative according to claim 1 or 2, wherein a transistion metal compound is employed as said metal catalyst.

4. A process for producing an α-aminonitrile derivative according to claim 1 or 2, wherein said metal catalyst comprises at least one element selected from the group consisting of the group 3A elements, the group 4A elements, the group 5A elements, the group 6A elements, the group 7A elements, the group 8 elements, the group 1B elements, the group 2B elements, and the group 3B elements of the Periodic Table of Elements.

5. A process for producing an α-aminonitrile derivative according to claim 1 or 2, wherein $R^1$ is a group selected from hydrogen atom, $C_{1-10}$alkyl groups, $C_{2-10}$alkenyl groups, $C_{3-10}$cycloalkyl groups, and $C_{6-10}$aryl groups.

6. A process for producing an α-aminonitrile derivative according to claim 1 or 2, wherein $R^2$ and $R^3$ are the same or different from each other and each represents a group selected from $C_{1-10}$alkyl groups, $C_{3-10}$cycloalkyl groups, and $C_{6-10}$aryl groups, or $R^2$ and $R^3$ form a 3 to 20-membered cycloalkane ring together with the adjacent carbon atom.

7. A process for producing an α-aminonitrile derivative according to claim 2, wherein $R^5$, $R^6$, and $R^7$ are the same or different from each other and each represents a group selected from hydrogen atom, $C_{1-10}$alkyl groups, $C_{3-10}$cycloalkyl groups, and $C_{6-10}$aryl groups.

8. A process for producing an α-aminonitrile derivative according to claim 2, wherein $R^5$, $R^6$, and $R^7$ are groups selected from hydrogen atom, $C_{1-6}$alkyl groups, and $C_{5-8}$cycloalkyl groups.

9. A process for producing an α-aminonitrile derivative according to claim 1 or 2, wherein said cyanogenation agent is a cyanogen compound selected from hydrogen cyanide, metal cyanides, cyanohydrin compounds, and acyl cyanides.

10. A process for producing an α-aminonitrile derivative according to claim 1 or 2, wherein said cyanogenation agent is a compound selected from hydrogen cyanide, cyanides of alkali metals and aliphatic α-cyanohydrins having 3 to 8 carbon atoms.

11. A process for producing an α-aminonitrile derivative according to claim 1, wherein the amount of said cyanogenation agent is not less than 0.8 mole relative to 1 mole of said oxime ester compound (1).

12. A process for producing an α-aminonitrile derivative according to claim 1, wherein the amount of said metal catalyst is 0.001 to 1 mole relative to 1 mole of said oxime ester compound (1).

13. A process for producing an α-aminonitrile derivative according to claim 2, wherein the ratio of said enol ester compound (3) to said oxime compound (4) is the former/the latter (molar ratio)=1/5 to 5/1.

14. A process for producing an α-aminonitrile derivative according to claim 2, wherein the amount of said cyanogenation agent is not less than 0.8 mole relative to 1 mole of said oxime compound (4).

15. A process for producing an α-aminonitrile derivative according to claim 2, wherein the amount of said metal catalyst is 0.001 to 1 mole relative to 1 mole of said oxime compound (4).

16. A process for producing an α-aminonitrile derivative, which comprises reacting, in the presence of a metal catalyst, (i) an oxime ester compound shown by the formula (1):

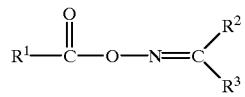

(1)

wherein $R^1$ represents a hydrogen atom, a $C_{1-6}$alkyl group, a $C_{2-6}$alkenyl group, a $C_{6-10}$aryl group, or a $C_{5-8}$cycloalkyl group; $R^2$ and $R^3$ are the same or different from each other and each represents a $C_{1-6}$alkyl group, a $C_{6-10}$aryl group, or a $C_{5-8}$cycloalkyl group; and $R^2$ and $R^3$, together with the adjacent carbon atom, may bond together to form a 3 to 16-membered ring (ii) with a cyanogenation agent having the formula $R^4CN$ to form an α-aminonitrile derivative shown by the formula (2):

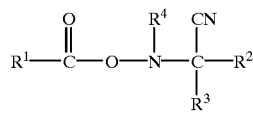

(2)

wherein $R^4$ represents the residue $R^4$ of the cyanogenation agent $R^4CN$; and $R^1$, $R^2$, $R^3$, and $R^4$ have the same meanings as defined above.

17. A process for producing an α-aminonitrile derivative according to claim 16, wherein the amount of said cyanogenation agent is 0.8 to 5 mole, and the amount of said metal catalyst is 0.01 to 0.5 mole, relative to 1 mole of said oxime ester compound (1).

18. A process for producing an α-aminonitrile derivative, which comprises reacting, in the presence of a metal catalyst, (i) an enol ester compound shown by the formula (3):

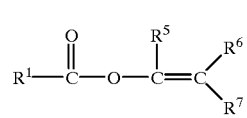

(3)

wherein $R^1$ represents a hydrogen atom, a $C_{1-6}$alkyl group, a $C_{2-6}$alkenyl group, a $C_{6-10}$aryl group, or a $C_{5-8}$cycloalkyl group; and $R^5$, $R^6$, and $R^7$ are the same or different from each other and each represents a hydrogen atom or a $C_{1-3}$alkyl group (ii) with an oxime compound shown by the formula (4):

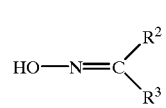

(4)

wherein $R^2$ and $R^3$ are the same or different from each other and each represents a $C_{1-6}$alkyl group, a $C_{6-10}$aryl group, or a $C_{5-8}$cycloalkyl group; and $R^2$ and $R^3$, together with the adjacent carbon atom, may bond together to form a 3 to 16-membered ring and (iii) a cyanogenation agent having the formula $R^4CN$, to form an α-aminonitrile derivative shown by the formula (2):

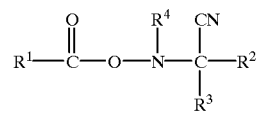

(2)

wherein $R^4$ represents the residue $R^4$ of the cyanogenation agent $R^4CN$; and $R^1$, $R^2$, $R^3$ and $R^4$ have the same meanings as defined above.

19. A process for producing an α-aminonitrile derivative according to claim 18, wherein the ratio of said enol ester compound (3) to said oxime compound (4) is the former/the latter (molar ratio)=1/2 to 2/1, the amount of said cyanidation agent is 0.8 to 5 mole, and the amount of metal catalyst is 0.01 to 0.5 mole, relative to 1 mole of said oxime compound (4).

20. A process for producing an α-amino acid shown by the formula (5):

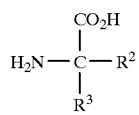

(5)

wherein $R^2$ and $R^3$ are the same or different from each other and each represents a non-reactive atom or a non-reactive organic group; and $R^2$ and $R^3$, together with the adjacent carbon atom, may bond together to form a ring or a or a salt thereof, which comprises (i) reacting, in the presence of a metal catalyst, an oxime ester compound shown by the formula (1):

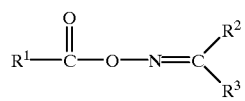
(1)

wherein $R^1$, $R^2$, and $R^3$ are the same or different from each other and each represents a non-reactive atom or a non-reactive organic group; and $R^2$ and $R^3$, together with the adjacent carbon atom, may bond together to form a ring (ii) with a cyanogenation agent having the formula $R^4CN$ to form an α-aminonitrile derivative shown by the formula (2):

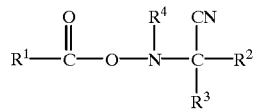
(2)

wherein $R^4$ represents the residue $R^4$ of the cyanogenation agent $R^4CN$; and $R^1$, $R^2$, and $R^3$ have the same meanings as defined above and $R^4CN$ comprises hydrogen cyanide, a metal cyanide, an acyl cyanide, a cyanohydrin compound, or a cyanogen halide, and (ii) hydrolyzing said α-aminonitrile derivative shown by the formula (2):

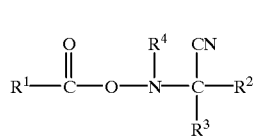
(2)

wherein $R^1$, $R^2$, $R^3$, and $R^4$ have the same meanings as defined above.

21. A process according to claim 1, or claim 20, further comprising a cyanohydrin of the formula $R^4CN$, wherein $R^8$ represents a hydroxyalkyl group, a cycloalkyl-hydroxyalkyl group, and an aryl-hydroxyalkyl group.

* * * * *